United States Patent
Finan (10) Patent No.: US 9,757,510 B2
(45) Date of Patent: Sep. 12, 2017

(54) METHOD AND SYSTEM TO HANDLE MANUAL BOLUSES OR MEAL EVENTS FOR CLOSED-LOOP CONTROLLERS

(75) Inventor: Daniel Finan, Philadelphia, PA (US)

(73) Assignee: Animas Corporation, West Chester, PA (US)

( * ) Notice: Subject to any disclaimer, the term of this patent is extended or adjusted under 35 U.S.C. 154(b) by 325 days.

(21) Appl. No.: 13/539,056

(22) Filed: Jun. 29, 2012

(65) Prior Publication Data

US 2014/0005633 A1    Jan. 2, 2014

(51) Int. Cl.
| | |
|---|---|
| A61M 31/00 | (2006.01) |
| A61M 5/142 | (2006.01) |
| A61M 5/172 | (2006.01) |
| G06F 19/00 | (2011.01) |

(52) U.S. Cl.
CPC ...... *A61M 5/14244* (2013.01); *A61M 5/1723* (2013.01); *G06F 19/3468* (2013.01); *A61M 2005/14208* (2013.01); *A61M 2209/01* (2013.01); *A61M 2230/005* (2013.01); *A61M 2230/201* (2013.01)

(58) Field of Classification Search
CPC .............. A61M 5/168; A61M 5/14244; A61M 5/1723; A61M 2230/005; A61M 2230/201; A61M 2005/14208; A61M 2209/01; G06F 19/3468
USPC ............ 604/890.1, 48, 65–67, 503–504, 506
See application file for complete search history.

(56) References Cited

U.S. PATENT DOCUMENTS

| | | | |
|---|---|---|---|
| 7,060,059 B2 | 6/2006 | Keith et al. | |
| 7,276,029 B2 | 10/2007 | Goode, Jr. et al. | |
| 2004/0152622 A1* | 8/2004 | Keith et al. | 514/3 |
| 2008/0183060 A1 | 7/2008 | Steil et al. | |

(Continued)

FOREIGN PATENT DOCUMENTS

| | | |
|---|---|---|
| RU | 83694 U1 | 6/2009 |
| WO | 2010099313 A1 | 9/2010 |
| WO | 2012051344 A2 | 4/2012 |

OTHER PUBLICATIONS

Percival et al., "Closed-Loop Control and Advisory Mode Evaluation of an Artificial Pancreatic β Cell: Use of Proportional-Integral-Derivative Equivalent Model-Based Controllers" Journal of Diabetes Science and Technology, vol. 2, Issue 4, Jul. 2008.

(Continued)

*Primary Examiner* — Kevin C Sirmons
*Assistant Examiner* — Tiffany Legette-Thompson (57) ABSTRACT

Described and illustrated is a diabetes management system that includes an infusion pump, glucose sensor and controller with a method programmed into the controller. The infusion pump is configured to deliver insulin to a subject. The glucose sensor is configured to sense glucose levels in the subject and provide output signals representative of the glucose levels in the subject. The controller is programmed to receive signals from at least one of the glucose sensor and the pump and configured to issue signals to the pump to deliver an amount of insulin determined by a feedback controller that utilizes a model predictive control and also configured to deliver at least the basal amount of insulin whenever the subject has initiated a manual bolus of insulin and a sensed or measured glucose level is at least a first threshold within a first duration of time.

10 Claims, 3 Drawing Sheets

(56) References Cited

U.S. PATENT DOCUMENTS

| | | | |
|---|---|---|---|
| 2008/0208113 | A1 | 8/2008 | Damiano et al. |
| 2010/0057043 | A1 | 3/2010 | Kovatchev et al. |
| 2010/0292557 | A1* | 11/2010 | Pesach et al. ............... 600/365 |
| 2010/0295686 | A1 | 11/2010 | Sloan et al. |
| 2010/0298685 | A1 | 11/2010 | Hayter et al. |
| 2010/0298765 | A1* | 11/2010 | Budiman ............ A61B 5/14532 604/66 |
| 2011/0106011 | A1* | 5/2011 | Cinar et al. ................... 604/151 |
| 2011/0130746 | A1* | 6/2011 | Budiman ............ A61B 5/14532 604/890.1 |
| 2011/0184380 | A1* | 7/2011 | Starkweather et al. ...... 604/504 |
| 2011/0257627 | A1 | 10/2011 | Hovorka |
| 2011/0313680 | A1 | 12/2011 | Doyle, III et al. |
| 2012/0078067 | A1 | 3/2012 | Kovatchev et al. |

OTHER PUBLICATIONS

Paola Soru et al.., "MPC Based Artificial Pancreas; Strategies for Individualization and Meal Compensation" Annual Reviews in Control 36, p. 118-128 (2012).

Cobelli et al., "Artificial Pancreas: Past, Present, Future" Diabetes vol. 60, Nov. 2011.

Magni et al., "Run-to-Run Tuning of Model Predictive Control for Type 1 Diabetes Subjects: In Silico Trial" Journal of Diabetes Science and Technology, vol. 3, Issue 5, Sep. 2009.

Lee et al., "A Closed-Loop Artificial Pancreas Using Model Predictive Control and a Sliding Meal Size Estimator" Journal of Diabetes Science and Technology, vol. 3, Issue 5, Sep. 2009.

Lee et al., "A Closed-Loop Artificial Pancreas based on MPC: Human Friendly Identification and Automatic Meal Disturbance Rejection" Proceedings of the 17th World Congress, The International Federation of Automatic Control, Seoul Korea Jul. 6-11, 2008.

Magni et al., "Model Predictive Control of Type 1 Diabetes: An in Silico Trial" Journal of Diabetes Science and Technology, vol. 1, Issue 6, Nov. 2007.

Wang et al., "Automatic Bolus and Adaptive Basal Algorithm for the Artificial Pancreatic β-Cell" Diabetes Technology and Therapeutics, vol. 12, No. 11, 2010.

Percival et al.., "Closed-Loop Control of an Artificial Pancreatic β-Cell Using Multi-Parametric Model Predictive Control" Diabetes Research 2008.

Maciejowski JM. "Predictive Control with Constraints." Harlow, UK: Prentice-Hall, Pearson Education Limited, 2002, pp. 156-158.

Rachel Gillis et al., "Glucose Estimation and Prediction through Meal Responses Using Ambulatory Subject Data for Advisory Mode Model Predictive Control" Journal of Diabetes Science and Technology vol. 1, Issue 6, Nov. 2007.

Youqing Wang et al., "Closed-Loop Control of Artificial Pancreatic β-Cell in Type 1 Diabetes Mellitus Using Model Predictive Iterative Learning Control" IEEE Transactions on Biomedical Engineering, vol. 57, No. 2, Feb. 2010.

Seborg DE, Edgar TF, Mellichamp DA, and Doyle III FJ. "Process Dynamics and Control." Hoboken, NJ: John Wiley & Sons, 2011, p. 401.

International Patent Application PCT/US2013/046260, PCT International Search Report and Written Opinion, 5 pages, dated Oct. 8, 2013.

International Preliminary Report on Patentability issued in International Patent Application No. PCT/US2013/046260, dated Dec. 31, 2014, 5 pages.

Official Action and Search Report issued in related Russian Patent Application No. 2015102842, received Apr. 27, 2017, 13 pages.

Notification of Reason for Refusal issued in related Japanese Patent Application No. 2015-520280, dated Mar. 21, 2017, 7 pages. (Prey Submitted on Jun. 19, 2017 (Fee Paid Jun. 22, 2017)).

\* cited by examiner

METHOD AND SYSTEM TO HANDLE MANUAL BOLUSES OR MEAL EVENTS FOR CLOSED-LOOP CONTROLLERS

BACKGROUND

Diabetes mellitus is a chronic metabolic disorder caused by an inability of the pancreas to produce sufficient amounts of the hormone insulin, resulting in the decreased ability of the body to metabolize glucose. This failure leads to hyperglycemia, i.e. the presence of an excessive amount of glucose in the blood plasma. Persistent hyperglycemia and/or hypoinsulinemia has been associated with a variety of serious symptoms and life threatening long term complications such as dehydration, ketoacidosis, diabetic coma, cardiovascular diseases, chronic renal failure, retinal damage and nerve damages with the risk of amputation of extremities. Because restoration of endogenous insulin production is not yet possible, a permanent therapy is necessary which provides constant glycemic control in order to always maintain the level of blood glucose within normal limits. Such glycemic control is achieved by regularly supplying external insulin to the body of the patient to thereby reduce the elevated levels of blood glucose.

External biologic such as insulin was commonly administered by means of multiple daily injections of a mixture of rapid and intermediate acting drug via a hypodermic syringe. It has been found that the degree of glycemic control achievable in this way is suboptimal because the delivery is unlike physiological hormone production, according to which hormone enters the bloodstream at a lower rate and over a more extended period of time. Improved glycemic control may be achieved by the so-called intensive hormone therapy which is based on multiple daily injections, including one or two injections per day of long acting hormone for providing basal hormone and additional injections of rapidly acting hormone before each meal in an amount proportional to the size of the meal. Although traditional syringes have at least partly been replaced by insulin pens, the frequent injections are nevertheless very inconvenient for the patient, particularly those who are incapable of reliably self-administering injections.

Substantial improvements in diabetes therapy have been achieved by the development of the drug delivery device, relieving the patient of the need for syringes or drug pens and the administration of multiple daily injections. The drug delivery device allows for the delivery of drug in a manner that bears greater similarity to the naturally occurring physiological processes and can be controlled to follow standard or individually modified protocols to give the patient better glycemic control.

In addition, delivery directly into the intraperitoneal space or intravenously can be achieved by drug delivery devices. Drug delivery devices can be constructed as an implantable device for subcutaneous arrangement or can be constructed as an external device with an infusion set for subcutaneous infusion to the patient via the transcutaneous insertion of a catheter, cannula or a transdermal drug transport such as through a patch. External drug delivery devices are mounted on clothing, hidden beneath or inside clothing, or mounted on the body and are generally controlled via a user interface built-in to the device or on a separate remote device.

Blood or interstitial analyte monitoring is required to achieve acceptable glycemic control. For example, delivery of suitable amounts of insulin by the drug delivery device requires that the patient frequently determines his or her blood analyte level and manually input this value into a user interface for the external pumps, which then calculates a suitable modification to the default or currently in-use insulin delivery protocol, i.e. dosage and timing, and subsequently communicates with the drug delivery device to adjust its operation accordingly. The determination of blood analyte concentration is typically performed by means of an episodic measuring device such as a hand-held electronic meter which receives blood samples via enzyme-based test strips and calculates the blood analyte value based on the enzymatic reaction.

Continuous analyte monitoring (CGM) has also been utilized over the last twenty years with drug delivery devices to allow for closed loop control of the insulin(s) being infused into the diabetic patients. To allow for closed-loop control of the infused insulins, proportional-integral-derivative (PID) controllers have been utilized with mathematical model of the metabolic interactions between glucose and insulin in a person. The PID controllers can be tuned based on simple rules of the metabolic models. However, when the PID controllers are tuned or configured to aggressively regulate the blood glucose levels of a subject, overshooting of the set level can occur, which is often followed by oscillations, which is highly undesirable in the context of regulation of blood glucose. Alternative controllers were investigated. It was determined that a model predictive controller (MPC) used in the petrochemical industries where processes involved large time delays and system responses, was the most suitable for the complex interplay between insulin, glucagon, and blood glucose. The MPC controller has been demonstrated to be more robust than PID because MPC considers the near future effects of control changes and constraints in determining the output of the MPC whereas PID typically involves only past outputs in determining future changes. Constraints can be implemented in the MPC controller such that MPC prevents the system from running away when the limit has already been reached. Another benefit of MPC controllers is that the model in the MPC can, in some cases, theoretically compensate for dynamic system changes whereas a feedback control, such as PID control, such dynamic compensation would not be possible.

MPC can be viewed therefore as a combination of feedback and feed forward control. MPC, however, typically requires a metabolic model to mimic as closely as possible to the interaction between insulin and glucose in a biological system. As such, due to person-to-person biological variations, MPC models continue to be further refined and developed and details of the MPC controllers, variations on the MPC and mathematical models representing the complex interaction of glucose and insulin are shown and described in the following documents:

U.S. Pat. No. 7,060,059;
US Patent Application Nos. 2011/0313680 and 2011/0257627,
International Publication WO 2012/051344,
Percival et al., "*Closed-Loop Control and Advisory Mode Evaluation of an Artificial Pancreatic β Cell: Use of Proportional-Integral-Derivative Equivalent Model-Based Controllers*" Journal of Diabetes Science and Technology, Vol. 2, Issue 4, July 2008.
Paola Soru et al., "*MPC Based Artificial Pancreas; Strategies for Individualization and Meal Compensation*" Annual Reviews in Control 36, p. 118-128 (2012),
Cobelli et al., "*Artificial Pancreas: Past, Present, Future*" Diabetes Vol. 60, November 2011;

Magni et al., "*Run-to-Run Tuning of Model Predictive Control for Type 1 Diabetes Subjects: In Silico Trial*" Journal of Diabetes Science and Technology, Vol. 3, Issue 5, September 2009.

Lee et al., "*A Closed-Loop Artificial Pancreas Using Model Predictive Control and a Sliding Meal Size Estimator*" Journal of Diabetes Science and Technology, Vol. 3, Issue 5, September 2009;

Lee et al., "*A Closed-Loop Artificial Pancreas based on MPC: Human Friendly Identification and Automatic Meal Disturbance Rejection*" Proceedings of the 17th World Congress, The International Federation of Automatic Control, Seoul Korea Jul. 6-11, 2008;

Magni et al., "*Model Predictive Control of Type 1 Diabetes: An in Silico Trial*" Journal of Diabetes Science and Technology, Vol. 1, Issue 6, November 2007;

Wang et al., "*Automatic Bolus and Adaptive Basal Algorithm for the Artificial Pancreatic β-Cell*" Diabetes Technology and Therapeutics, Vol. 12, No. 11, 2010; and Percival et al., "*Closed-Loop Control of an Artificial Pancreatic β-Cell Using Multi-Parametric Model Predictive Control*" Diabetes Research 2008.

All articles or documents cited in this application are hereby incorporated by reference into this application as if fully set forth herein.

SUMMARY OF THE DISCLOSURE

Applicants have identified a counterproductive effect of some realizations of model-based control (including MPC) that fail to account for the effects of meals or a combination of meals and manual boluses. In such a scenario, the model in the MPC may predict a quiescent, steady glucose trend for the near future, even immediately after the subject or patient ingested a snack or meal containing a substantial amount of carbohydrates. In this scenario, it is likely that the model's prediction of future glucose is erroneous due to the model's failure to account for effects of the snack. Applicants have also identified that the model's failure may be further exacerbated in the same scenario but with the subject giving a self-delivered or manual bolus to account for the snack. Because the manual bolus can be recognized by the model (due to pump configuration) but the snack cannot, the controller may reduce or even suspend insulin infusion after the manual bolus. This post-bolus attenuation of insulin infusion by the controller is believed to be counterproductive because it effectively negates a portion of the manual bolus. From an identification of the shortcoming of such closed-loop control, applicants have devised a solution to mitigate such counterproductive effect of the closed-loop (e.g., MPC) control.

In one aspect of the solution, applicants have provided a diabetes management system that includes an infusion pump, glucose sensor and controller. The infusion pump is configured to deliver insulin to a subject. The glucose sensor is configured to sense glucose levels in the subject and provide output signals representative of the glucose levels in the subject.

The controller receives signals from at least one of the glucose sensor and the pump, and configured to issue signals to the pump to deliver an amount of insulin determined by a feedback controller that utilizes a model predictive control of the subject based on desired glucose levels, insulin amount delivered and measured glucose levels of the subject. The controller is configured to deliver at least the basal amount of insulin whenever the subject has initiated a manual bolus of insulin and a sensed or measured glucose level of is at least a first threshold within a first duration of time.

That is, the controller is provided with constraints to deliver at least the basal quantity of insulin whenever the subject has initiated a manual bolus of insulin and a sensed or measured glucose level of is at least a first threshold within a first duration of time. In this aspect, the first threshold may be about 120 milligrams of glucose per deciliter of blood and the first duration may be from about 15 minutes to about 240 minutes. Further, the glucose sensor may include at least one of an episodic glucose sensor and a continuous glucose sensor.

In yet another aspect of the solution devised by applicants, a method to manage diabetes for a subject with an infusion pump, controller, and glucose sensor is provided. The method can be achieved by: measuring glucose level in the subject from the glucose sensor to provide a plurality of glucose measurements; calculating insulin amount by the controller for delivery based on a model predictive controller that utilizes the plurality of glucose measurements to predict a trend of the glucose level from estimates of a metabolic state of the subject so as to provide a calculated insulin amount to be delivered to the subject over a predetermined interval; determining whether the subject initiated a manual bolus while the glucose level is at least a first glucose threshold within a first time period; and in the event the determining step is true, constraining insulin delivery to be at least the basal amount. In the above aspects, the first glucose threshold may include a glucose concentration of any concentration from about 80 mg of glucose per deciliter of blood to about 180 mg of glucose per deciliter of blood; the first time period may include a duration of any value from about 15 minutes to two hours; the predetermined interval may include an interval selected from a group consisting essentially of 1 minute, 3, minutes, 5 minutes, 10 minutes, 15 minutes, 20 minutes, 30 minutes and combinations thereof. In this method, the glucose sensor may include at least one of an episodic glucose sensor and a continuous glucose sensor. In this aspect, the calculating further may include recursively determining an estimate of a metabolic state of the subject from approximately real-time measurements of the glucose levels in the subject.

In a further aspect, a method to manage diabetes for a subject with an infusion pump, controller, and glucose sensor is provided. The method can be achieved by: measuring glucose level in the subject from the glucose sensor to provide a plurality of glucose measurements; calculate a basal rate for delivery to the subject; determining whether the subject initiated a manual bolus with the glucose level being at a level of at least a first glucose threshold within a first time period; in the event the determining is true, constraining the infusion pump to deliver insulin at the basal rate; in the event the determining is false, limiting the infusion pump to deliver at approximately zero rate; calculating insulin dosing based on the constraining and limiting steps; and commanding the pump to deliver insulin dosing calculated by the calculating step. In the above aspects, the first glucose threshold may include a glucose concentration of any concentration from about 80 mg of glucose per deciliter of blood to about 180 mg of glucose per deciliter of blood; the first time period may include a duration of any value from about 15 minutes to two hours; the predetermined interval may include an interval selected from a group consisting essentially of 1 minute, 3, minutes, 5 minutes, 10 minutes, 15 minutes, 20 minutes, 30 minutes and combinations thereof. In this method, the glucose sensor may include at least one of an episodic glucose sensor and a continuous glucose sensor. Additionally, the calculating further may include recursively determining an estimate of a metabolic state of the subject from approximately real-time measurements of the glucose levels in the subject.

These and other embodiments, features and advantages will become apparent to those skilled in the art when taken with reference to the following more detailed description of various exemplary embodiments of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

MODES FOR CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. In addition, as used herein, the terms "patient," "host," "user," and "subject" refer to any human or animal subject and are not intended to limit the systems or methods to human use, although use of the subject invention in a human patient represents a preferred embodiment. Furthermore, the term "user" includes not only the patient using a drug infusion device but also the caretakers (e.g., parent or guardian, nursing staff or home care employee). The term "drug" may include hormone, biologically active materials, pharmaceuticals or other chemicals that causes a biological response (e.g., glycemic response) in the body of a user or patient.

Figure 1:
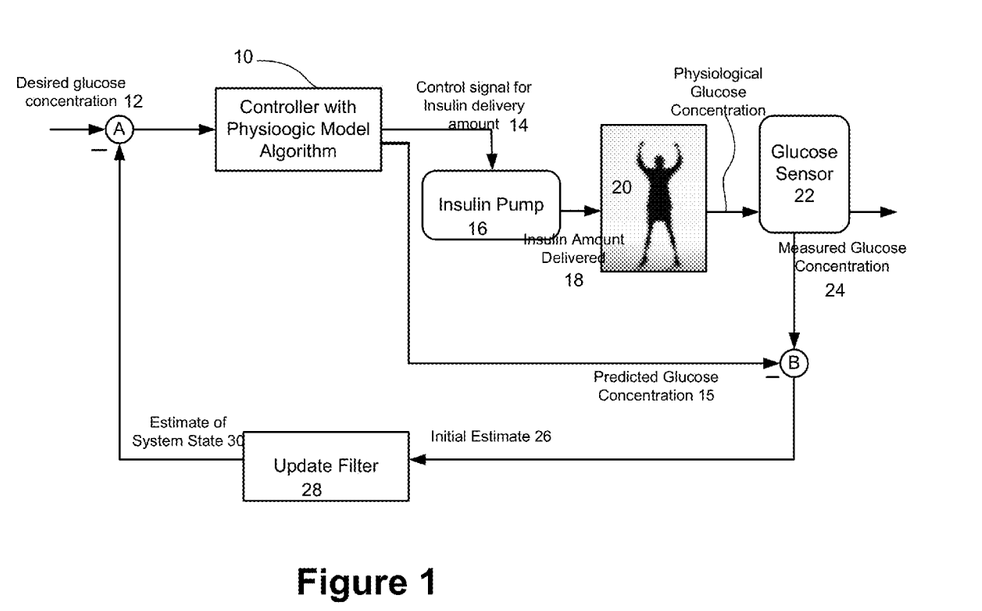
FIG. 1 illustrates an exemplary embodiment of the diabetic management system in schematic form.

FIG. 1 illustrates a schematic diagram of a system programmed with the solution devised by applicants to counteract a less than desirable effect of a closed-loop control system. In particular, FIG. 1 provides for a controller 10 that receives a desired glucose concentration or range of glucose concentration 12 (along with any modification from an update filter 28). The controller 10 is programmed with an appropriate MPC to maintain the output (i.e., glucose level) of the subject within the desired range of levels.

Referring to FIG. 1, the first output 14 of the MPC-enabled controller 10 can be a control signal to an insulin pump 16 to deliver a desired quantity of insulin 18 into a live subject 20 at predetermined time intervals. A second output in the form of a predicted glucose value 15 can be utilized in control junction B. A glucose sensor 22 measures the glucose levels in the subject 20 in order to provide signals 24 representative of the actual or measured glucose levels to control junction B, which takes the difference between measured glucose concentration 24 and the MPC predictions of that measured glucose concentration. This difference provides input for the update filter 26 of state variables of the model. The difference 26 is provided to an estimator (also known as an update filter 28) that provides for estimate of state variables of the model that cannot be measured directly. The update filter 28 is preferably a recursive filter in the form of a Kalman filter with tuning parameters for the model. The output of the update or recursive filter 28 is provided to control junction A whose output is utilized by the MPC in the controller 10 to further refine the control signal 14 to the pump 16. A brief overview of the MPC used in controller 10 is provided below.

The MPC of controller 10 incorporates an explicit model of human T1DM glucose-insulin dynamics. The model is used to predict future glucose values and to calculate future controller moves that will bring the glucose profile to the desired range. MPC controllers can be formulated for both discrete- and continuous-time systems; the controller is set in discrete time, with the discrete time (stage) index k referring to the epoch of the $k^{th}$ sample occurring at continuous time $t=k \cdot T_s$, where $T_s=5$ min is the sampling period. Software constraints ensure that insulin delivery rates are constrained between minimum (i.e., zero) and maximum values. The first insulin infusion (out of N steps) is then implemented. At the next time step, k+1 based on the new measured glucose value and the last insulin rate, the process is repeated.

The MPC algorithm is formulated to control to a safe glucose zone, with the lower limit of the zone varying between 80-100 mg/dL and the upper limit varying between about 140-180 mg/dL; the algorithm will henceforth be referred to as the "zone MPC" algorithm. Controlling to a target zone is, in general, applied to controlled systems that lack a specific set point with the controller goal to keep the controlled variable (CV) in a predefined zone. Control to zone (i.e. a normaglycemic zone) is highly suitable for the artificial pancreas because of the absence of a natural glycemic set point. Moreover, an inherent benefit of control to zone is limiting pump actuation/activity in a way that if glucose levels are within the zone no extra correction shall be suggested.

In real-time, the insulin delivery rate $I_D$ from the zone MPC law is calculated by an on-line optimization, which evaluates at each sampling time the next insulin delivery rate. The optimization at each sampling time is based on the estimated metabolic state (plasma glucose, subcutaneous insulin) obtained from the dynamic model.

Using the FDA-accepted UVa/Padova metabolic simulator a reduced linear difference model was obtained which relates the effects of insulin infusion rate ($I_D$), and CHO ingestion input (Meal) on plasma glucose. The model represents a single average model for the total population of subjects. The model and its parameters are fixed.

The model includes second-order input transfer functions that are used to generate an artificial input memory in the zone MPC schema to prevent insulin over-dosing, and as a result hypoglycemia. In order to avoid over-delivery of insulin, the evaluation of any sequential insulin delivery must take into consideration the past administered insulin against the length of the insulin action. However, a one-state linear difference model with a relatively low order uses the output (glycemia) as the main source of past administered input (insulin) "memory." In the face of the model mismatch, noise, or change in the subject's insulin sensitivity, this may result in under- or over-delivery of insulin. This is mitigated by adding two additional states for the mapped insulin and meal inputs that carry a longer insulin memory. In this system, the insulin delivery rates $I_D$ are adjusted over a finite horizon of M control moves, with the predicted outputs G given by the model over a control horizon of P samples, assuming the insulin delivery rate stays constant after time M until time P. Deviations in the estimated plasma glucose outside the target zone and insulin delivery rates from the basal rate (for that time of day) are penalized by the parameters Q and R, respectively.

Zone MPC is applied when the specific set point value of a controlled variable (CV) is of low relevance compared to a zone that is defined by upper and lower boundaries. Moreover, in the presence of noise and model mismatch there is no practical value using a fixed set point. A related derivation of zone MPC was presented in Maciejowski J M. *Predictive control with constraints*. Harlow, UK: Prentice-Hall, Pearson Education Limited, 2002.

The zone MPC is implemented by defining fixed upper and lower bounds as soft constraints by letting the optimization weights switch between zero and some final values when the predicted CVs are in or out of the desired zone, respectively. The predicted residuals are generally defined as the difference between the CV that is out of the desired zone and the nearest bound. Zone MPC is typically divided into three different zones. The permitted range is the control target and it is defined by upper and lower bounds. The upper zone represents undesirable high predicted glycemic values. The lower zone represents undesirable low predicted glycemic values that represent hypoglycemic zone or a pre-hypoglycemic protective area that is a low alarm zone. The zone MPC optimizes the predicted glycemia by manipulating the near-future insulin control moves to stay in the permitted zone under specified constrains.

The core of zone MPC lies in its cost function formulation that holds the zone formulation. Zone MPC, like any other forms of MPC, predicts the future output by an explicit model using past input/output records and future input moves that need to be optimized. However, instead of driving to a specific fixed set point, the optimization attempts to keep or move the predicted outputs into a zone that is defined by upper and lower bounds. Using a linear difference model, the glycemic dynamics are predicted and the optimization reduces future glycemic excursions from the zone under constraints and weights defined in its cost function.

A suitable technical computing software (e.g., MATLAB 'fmincon.m') is used to solve the optimization problem described above and the following hard constraints are implemented on the manipulated variables ($I_D'$): $-basal \leq I_D' \leq 72$ U/h
where the subject's basal rate (as set by the subject's physician) is expected to be in the range of about 0.6 U/hr to 1.8 U/hr.

Once the controller is initialized and switched on, real-time calculations take place every five minutes, corresponding to the sample time for the glucose sensor. Initialization corresponds to gathering enough information about prior glucose measurements and insulin delivery rates, such that the model can make predictions about future glucose concentrations.

Although the values of parameters M and P have significant effects on the controller performance, and are normally used to tune an MPC based controller, they can be heuristically tuned based on knowledge of the system. Tuning rules are given on pages 555-556 of Seborg D E, Edgar T F, and Mellichamp D A *"Process dynamics and control"* Hoboken, N.J.: John Wiley & Sons, 2004. According to these rules, M and P may be varied between 2 and 10 for M and 20 and 120 for P with preference for M~5 and P~108. The ratio of the output error weighting matrix (Q) and the input change weighting matrix (R) may varied between 10 and 1000 with preference for R/Q~500.

Other details of related subject matter including state estimator, and other MPC are provided by Rachel Gillis et al., *"Glucose Estimation and Prediction through Meal Responses Using Ambulatory Subject Data for Advisory Mode Model Predictive Control"* Journal of Diabetes Science and Technology Vol. 1, Issue 6, November 2007 and by Youqing Wang et al., *"Closed-Loop Control of Artificial Pancreatic β-Cell in Type 1 Diabetes Mellitus Using Model Predictive Iterative Learning Control"* IEEE Transactions on Biomedical Engineering, Vol. 57, No. 2, February 2010, which are hereby incorporated by reference into this application as if fully set forth herein.

Figure 2:
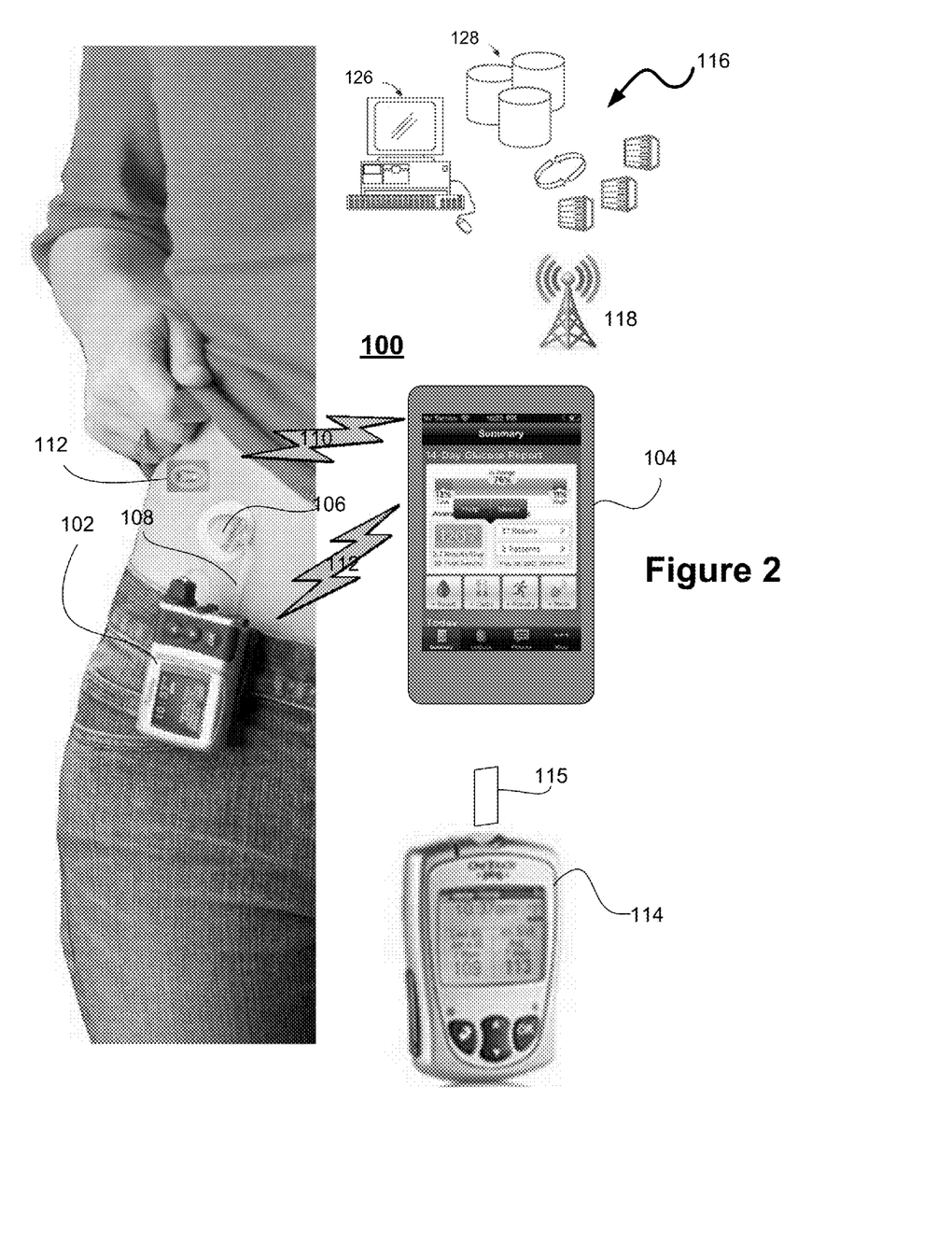
FIG. 2 illustrates the infusion set for the system of FIG. 1 in which a controller for the pump or glucose monitor(s) is separate from both the infusion pump and the glucose monitor(s) and in which a network can be coupled to the controller to provide near real-time monitoring.

FIG. 2 illustrates a drug delivery system 100 according to an exemplary embodiment. Drug delivery system 100 includes a drug delivery device 102 and a remote controller 104. Drug delivery device 102 is connected to an infusion set 106 via flexible tubing 108.

Drug delivery device 102 is configured to transmit and receive data to and from remote controller 104 by, for example, radio frequency communication 112. Drug delivery device 102 may also function as a stand-alone device with its own built in controller. In one embodiment, drug delivery device 102 is an insulin infusion device and remote controller 104 is a hand-held portable controller. In such an embodiment, data transmitted from drug delivery device 102 to remote controller 104 may include information such as, for example, insulin delivery data, blood glucose information, basal, bolus, insulin to carbohydrates ratio or insulin sensitivity factor, to name a few. The controller 104 is configured to include an MPC controller that has been programmed to receive continuous analyte readings from a CGM sensor 112. Data transmitted from remote controller 104 to insulin delivery device 102 may include analyte test results and a food database to allow the drug delivery device 102 to calculate the amount of insulin to be delivered by drug delivery device 102. Alternatively, the remote controller 104 may perform basal dosing or bolus calculation and send the results of such calculations to the drug delivery device. In an alternative embodiment, an episodic blood analyte meter 114 may be used alone or in conjunction with the CGM sensor 112 to provide data to either or both of the controller 104 and drug delivery device 102. Alternatively, the remote controller 104 may be combined with the meter 114 into either (a) an integrated monolithic device; or (b) two separable devices that are dockable with each other to form an integrated device. Each of the devices 102, 104, and 114 has a suitable micro-controller (not shown for brevity) programmed to carry out various functionalities.

Drug delivery device 102 may also be configured for bi-directional wireless communication with a remote health monitoring station 116 through, for example, a wireless communication network 118. Remote controller 104 and remote monitoring station 116 may be configured for bi-directional wired communication through, for example, a telephone land based communication network. Remote monitoring station 116 may be used, for example, to download upgraded software to drug delivery device 102 and to process information from drug delivery device 102. Examples of remote monitoring station 116 may include, but are not limited to, a personal or networked computer 126, server 128 to a memory storage, a personal digital assistant, other mobile telephone, a hospital base monitoring station or a dedicated remote clinical monitoring station.

Drug delivery device 102 includes processing electronics including a central processing unit and memory elements for storing control programs and operation data, a radio frequency module 116 for sending and receiving communication signals (i.e., messages) to/from remote controller 104, a display for providing operational information to the user, a plurality of navigational buttons for the user to input information, a battery for providing power to the system, an alarm (e.g., visual, auditory or tactile) for providing feedback to the user, a vibrator for providing feedback to the user, a drug delivery mechanism (e.g. a drug pump and drive mechanism) for forcing a insulin from a insulin reservoir (e.g., a insulin cartridge) through a side port connected to an infusion set 108/106 and into the body of the user.

Analyte levels or concentrations can be determined by the use of the CGM sensor 112. The CGM sensor 112 utilizes amperometric electrochemical sensor technology to measure analyte with three electrodes operably connected to the sensor electronics and are covered by a sensing membrane and a biointerface membrane, which are attached by a clip.

The top ends of the electrodes are in contact with an electrolyte phase (not shown), which is a free-flowing fluid phase disposed between the sensing membrane and the electrodes. The sensing membrane may include an enzyme, e.g., analyte oxidase, which covers the electrolyte phase. In this exemplary sensor, the counter electrode is provided to balance the current generated by the species being measured at the working electrode. In the case of an analyte oxidase based analyte sensor, the species being measured at the working electrode is $H_2O_2$. The current that is produced at the working electrode (and flows through the circuitry to the counter electrode) is proportional to the diffusional flux of $H_2O_2$. Accordingly, a raw signal may be produced that is representative of the concentration of analyte in the user's body, and therefore may be utilized to estimate a meaningful analyte value. Details of the sensor and associated components are shown and described in U.S. Pat. No. 7,276,029, which is incorporated by reference herein as if fully set forth herein this application. In one embodiment, a continuous analyte sensor from the Dexcom Seven System (manufactured by Dexcom Inc.) can also be utilized with the exemplary embodiments described herein.

In one embodiment of the invention, the following components can be utilized as a diabetes management system that is akin to an artificial pancreas: OneTouch Ping® Glucose Management System by Animas Corporation that includes at least an infusion pump and an episodic glucose sensor; and DexCom® SEVEN PLUS® CGM by DexCom Corporation with interface to connect these components and programmed in MATLAB® language and accessory hardware to connect the components together; and control algorithms in the form of an MPC that automatically regulates the rate of insulin delivery based on the glucose level of the patient, historical glucose measurement and anticipated future glucose trends, and patient specific information.

Figure 3:
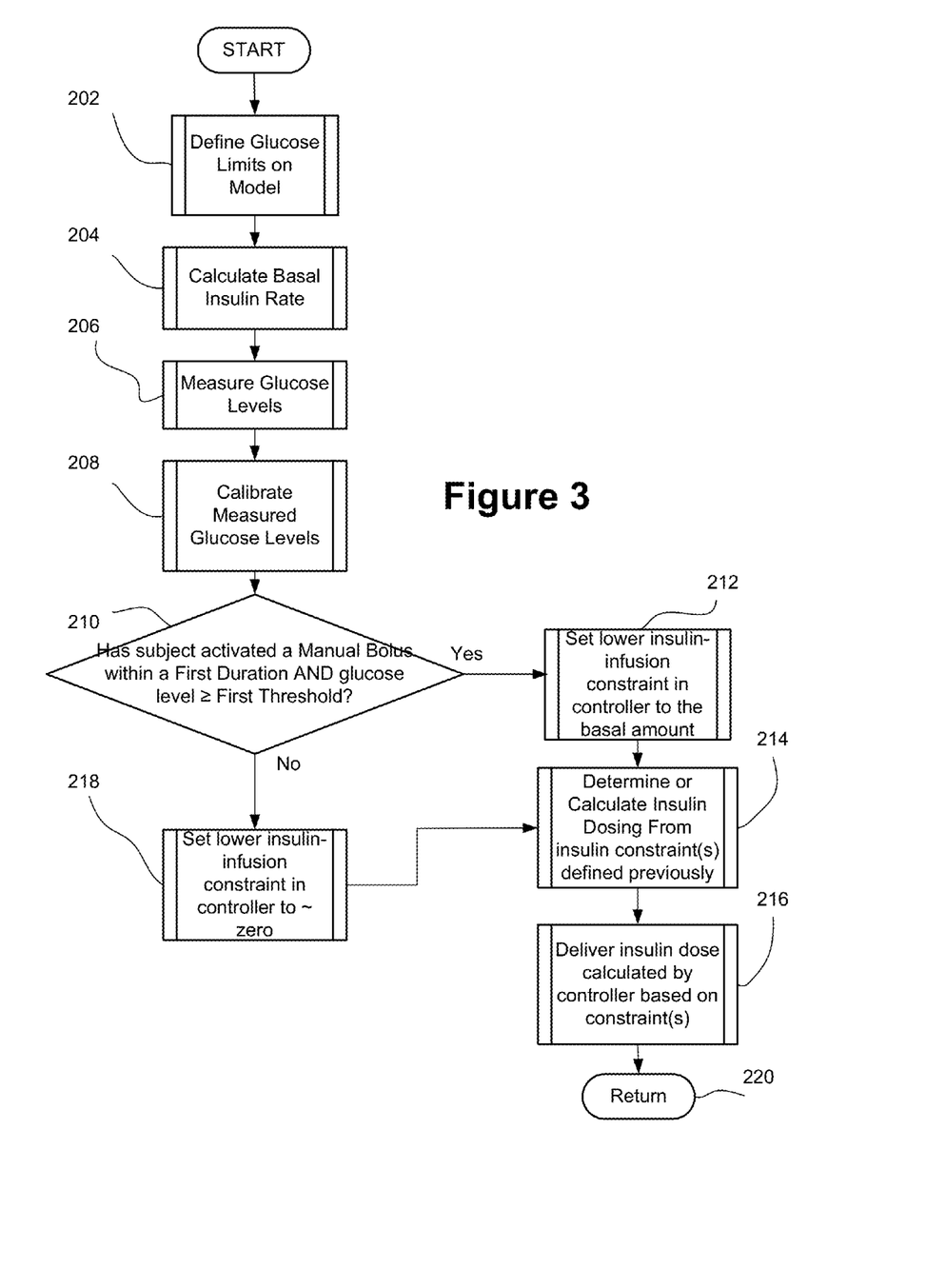
FIG. 3 illustrates the logic utilized in the controller of FIG. 1 or FIG. 2.

Applicants have recognized that in an MPC-based closed-loop controller that does not account for the effects of meals, the closed-loop controller may attenuate the delivery of insulin in a situation where the subject has manually delivered a bolus, thereby potentially causing the subject's blood glucose to exceed a desired threshold. With reference to FIG. 3, applicants have devised a method 200 that accounts for the manual bolus without necessitating extensive reconfiguration of the model utilized by the closed-loop controller 10. In particular, at step 202, the system is provided with a desired glucose range which the controller will dose insulin in order to achieve or maintain. The system in the form of a processor begins the logic 200 by calculating a basal insulin rate at step 204 based on at least one of the following variables: total daily insulin, overnight insulin rate, bodyweights, insulin sensitivity factor, carbohydrates ratio or from past basal insulin rate. The basal insulin rate is well known to those skilled in this art as shown and described in, for example, US Patent Application Publication No. 20120078067 "System Coordinator and Modular Architecture for Open-Loop and Closed-Loop Control of Diabetes"; US Patent Application Publication No. 20100295686 entitled "USABILITY FEATURES FOR INTEGRATED INSULIN DELIVERY SYSTEM"; or US Patent Application Publication No. 20100057043 entitled "Method, System, and Computer Program Product for the Detection of Physical Activity by Changes in Heart Rate, Assessment of Fast Changing Metabolic States, and Applications of Closed and Open Control Loop in Diabetes." Therefore for the sake of brevity, techniques for basal insulin determination need not be described further.

Referring back to FIG. 3, the processor also measures the glucose levels at step 206 from the subject in order to determine the appropriate insulin dosing due to external inputs (possibly unmeasured) to the subject such as food, stress, exercise. In the preferred embodiments, the measuring at step 206 is performed by a CGM and therefore at appropriate times, the system may remind the subject to calibrate the CGM with a different glucose monitor type at step 208. At step 210, the logic determines if the subject has activated a manual bolus within a first duration and the glucose level is greater than or equal to a first threshold. If true, the logic proceeds to step 212 set a lower infusion constraint in the controller to the basal amount and thereafter to step 214 to determine the appropriate insulin dose with the controller that would be provided by step 216. If, however, the query at step 210 is false, the logic proceeds to set a lower insulin-infusion constraint in the controller to approximately zero in step 218. Thereafter, the logic proceeds to step 214 for the controller to determine the appropriate insulin dosing, which would be delivered at step 216. It is noted that once the appropriate insulin dose has been determined at step 214 based on the constraint(s) from step 214 or step 218 (which is selected depending on the user's activation of a manual bolus and measured glucose level) the system proceeds to deliver the calculated insulin dosing. At step 220, the system returns to its main routine.

In the preferred embodiment, the first threshold can be from about 80 mg of glucose per deciliter of blood ("mg/dL") to about 180 mg/dL or its equivalent level found in interstitial fluid and the first duration can be any value from about 15 minutes to about two hours. In the most preferred embodiments, the first threshold is about 120 mg/dL and the first duration may be from about 15 minutes to about 240 minutes.

In operation, the logic ensures that if any attenuation of insulin delivery is contemplated by the system due to an unidentified meal or snack accompanied by a manual bolus, such attenuation is mitigated by having at least is the basal amount of insulin provided to the subject. This mitigation logic is believed to counteract any attenuation of insulin delivery by the closed loop controller whenever the controller detects a manual bolus. By incorporation of this mitigation logic, it is believed that a net benefit is provided to the subject by ensuring that the subject's glycemic state is within the desired range.

While the invention has been described in terms of particular variations and illustrative figures, those of ordinary skill in the art will recognize that the invention is not limited to the variations or figures described. For example, the closed-loop controller need not be an MPC controller but can be, with appropriate modifications by those skilled in the art, a PID controller, a PID controller with internal model control (IMC), a model-algorithmic-control (MAC) that are discussed by Percival et al., in "*Closed-Loop Control and Advisory Mode Evaluation of an Artificial Pancreatic β Cell: Use of Proportional-Integral-Derivative Equivalent Model-Based Controllers*" Journal of Diabetes Science and Technology, Vol. 2, Issue 4, July 2008. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A diabetes management system comprising:
    an infusion pump configured to deliver insulin to a subject;
    a glucose sensor configured to sense glucose levels in the subject and provide output signals representative of the glucose levels in the subject; and
    a controller that receives signals from at least one of the glucose sensor and the infusion pump, the controller configured to calculate a basal insulin rate and issue signals to the infusion pump to deliver an amount of insulin determined by a feedback controller that utilizes a model predictive control of the subject based on desired glucose levels, insulin amount delivered, and measured glucose levels of the subject, the controller being further configured to determine whether: (a) the subject has initiated a manual bolus of insulin using the infusion pump within a first duration, and (b) a sensed or measured glucose level from the glucose sensor is at least a first threshold wherein the controller is configured to set a first lower insulin-infusion constraint if the controller determines that the subject has initiated the manual bolus of insulin within the first duration and the glucose level is at least equal to or greater than a first predetermined threshold, the first lower insulin-infusion constraint being equal to the calculated basal insulin rate and to set a lower second infusion constraint of zero if the controller determines that the subject has activated the manual bolus within the duration of time and the glucose level is not greater than or equal to the predetermined threshold and in which the model predictive control determines the amount of insulin to deliver based on either the first or second infusion constraint and wherein model predictive control is continually maintained by the system.

2. The system of claim 1, in which the first threshold comprises about 120 milligrams of glucose per deciliter of blood and the first duration comprises about 45 minutes.

3. The system of claim 2, in which the glucose sensor comprises at least one of an episodic glucose sensor and a continuous glucose sensor.

4. A method to manage diabetes of a subject with an infusion pump, controller, and at least one glucose sensor, the method comprising:
    measuring glucose level in the subject from the at least one glucose sensor to provide a plurality of glucose measurements;
    calculating a basal insulin rate by the controller for delivery by an insulin pump based on a model predictive controller that utilizes the plurality of glucose measurements to predict a trend of the glucose level from estimates of a metabolic state of the subject so as to provide a calculated insulin amount relative to the calculated basal insulin rate to be delivered to the subject over a predetermined interval;
    determining, using the model predictive controller, whether the subject initiated a manual bolus using the insulin pump, while the measured glucose level is at least a first glucose threshold within a first time period;
    if the subject has initiated a manual bolus while the measured glucose is at least a first glucose threshold within the first time period, then using the model predictive controller, constraining insulin delivery to be proceeded for delivery at a first lower infusion constraint equal to the calculated basal insulin rate; and
    if the subject initiated the manual bolus within the duration of time and the measured glucose level is not greater than or equal to the predetermined threshold, using the model predictive controller to constrain insulin delivery to a second lower infusion constraint which is equal to zero,
    wherein the model predictive controller determines the insulin delivery.

5. A method to manage diabetes of a subject with an infusion pump, controller, and at least one glucose sensor, the method comprising:
    measuring glucose level in the subject from the glucose sensor to provide a plurality of glucose measurements;
    calculating a basal insulin rate for delivery of insulin to the subject based on a model predictive controller that utilizes the plurality of glucose measurements to predict a trend of the glucose level from estimates of a metabolic state of the subject so as to provide a calculated insulin amount to be delivered to the subject over a predetermined interval;
    determining using the model predictive controller whether (a) the subject initiated a manual bolus using the infusion pump with (b) the measured glucose level being at a level of at least a first glucose threshold within a first time period;
    in the event the subject initiated a manual bolus using the infusion pump and the measured glucose level is at a level of least the first glucose threshold within the first time period and using the model predictive controller, constraining the infusion pump to proceed with minimum delivery of insulin by the infusion pump at a first infusion constraint equal to the calculated basal insulin rate;

in the event the determining is false and using the model predictive controller, limiting the infusion pump to deliver at a second lower infusion constraint of approximately zero rate;

calculating insulin dosing with the model predictive controller based on the constraining and limiting steps; and commanding the pump to deliver insulin dosing calculated by the calculating step.

6. The method of one of claim 4 or 5, in which the first glucose threshold comprises a glucose concentration of any concentration from about 80 mg of glucose per deciliter of blood to about 180 mg of glucose per deciliter of blood.

7. The method of claim 6, in which the first time period comprises a duration of any value from about 15 minutes to two hours.

8. The method according to one of claim 4 or claim 5, in which the predetermined interval comprises an interval selected from a group consisting essentially of 1 minute, 3, minutes, 5 minutes, 10 minutes, 15 minutes, 20 minutes, 30 minutes and combinations thereof.

9. The method according to one of claim 4 or claim 5, in which the glucose sensor comprises at least one of an episodic glucose sensor and a continuous glucose sensor.

10. The method according to one of claim 4 or claim 5, in which the calculating further comprises recursively determining an estimate of a metabolic state of the subject from approximately real-time measurements of the glucose levels in the subject.

* * * * *